(12) United States Patent
Nguyen et al.

(10) Patent No.: US 12,740,762 B2
(45) Date of Patent: Sep. 22, 2026

(54) MULTI-PATCH ARRAY, ULTRASOUND SYSTEM, AND METHOD FOR OBTAINING AN EXTENDED FIELD OF VIEW

(71) Applicant: KONINKLIJKE PHILIPS N.V., Eindhoven (NL)

(72) Inventors: Man Nguyen, Melrose, MA (US); Shyam Bharat, Arlington, MA (US); Nico Maris Adriaan De Wild, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 444 days.

(21) Appl. No.: 16/478,144

(22) PCT Filed: Jan. 19, 2018

(86) PCT No.: PCT/EP2018/051332
§ 371 (c)(1),
(2) Date: Jul. 16, 2019

(87) PCT Pub. No.: WO2018/134364
PCT Pub. Date: Jul. 26, 2018

(65) Prior Publication Data

US 2019/0365351 A1 Dec. 5, 2019

Related U.S. Application Data

(60) Provisional application No. 62/448,030, filed on Jan. 19, 2017.

(51) Int. Cl.
*A61B 8/00* (2006.01)
*A61B 8/14* (2006.01)
(Continued)

(52) U.S. Cl.
CPC ............ *A61B 8/4461* (2013.01); *A61B 8/145* (2013.01); *A61B 8/4236* (2013.01);
(Continued)

(58) Field of Classification Search
CPC ..... A61B 8/4461; A61B 8/145; A61B 8/4236; A61B 8/4477; A61B 8/4494; A61B 34/20;
(Continued)

(56) References Cited

U.S. PATENT DOCUMENTS 4,437,468 A * 3/1984 Sorenson ............ A61B 8/0875 600/459
6,530,885 B1 3/2003 Entrekin
(Continued)

FOREIGN PATENT DOCUMENTS

WO 2016/038926 3/2016
WO 2016058963 4/2016

OTHER PUBLICATIONS

International Search Report and Written Opinion Dated Jul. 27, 2018 for International Application No. PCT/EP2018/051332 Filed Jan. 19, 2018.

*Primary Examiner* — Christopher Koharski
*Assistant Examiner* — Aminah Asghar

(57) ABSTRACT

A multi-patch ultrasound array according to the present disclosure includes a plurality of patches of transducer elements, the plurality of patches arranged along a first direction of the array, and a frame connecting the plurality of patches such that adjacent ones of the plurality of patches are slidable relative to one another in a second direction of the array which is perpendicular to the first direction.

20 Claims, 9 Drawing Sheets

(51) Int. Cl.
*A61B 34/20* (2016.01)
*G01S 15/89* (2006.01)
*H10N 30/02* (2023.01)

(52) U.S. Cl.
CPC .......... *A61B 8/4477* (2013.01); *A61B 8/4494* (2013.01); *A61B 34/20* (2016.02); *G01S 15/8927* (2013.01); *G01S 15/8945* (2013.01); *H10N 30/02* (2023.02); *A61B 2034/2051* (2016.02); *A61B 2034/2063* (2016.02)

(58) Field of Classification Search
CPC .... A61B 2034/2051; A61B 2034/2063; A61B 8/4227; A61B 8/5246; A61B 8/4209; A61B 8/0891; A61B 8/4245; G01S 15/8927; G01S 15/8945; G01S 15/8915; H01L 41/23; G01N 29/225
See application file for complete search history.

(56) References Cited

U.S. PATENT DOCUMENTS 9,078,593 B2* 7/2015 Southern .............. A61B 5/0048
9,282,946 B2 3/2016 Vignon
2002/0138074 A1* 9/2002 Keast ................. A61B 18/1485 606/41
2006/0058709 A1 3/2006 Mason
2007/0078345 A1* 4/2007 Mo .......................... A61B 8/12 600/459
2007/0167782 A1 7/2007 Callhan
2008/0304729 A1* 12/2008 Peszynski ............ A61B 8/4455 382/131
2009/0299193 A1* 12/2009 Haftman .............. G10K 11/355 600/459
2010/0063398 A1 3/2010 Halmann
2011/0224551 A1* 9/2011 Barnard ............... A61B 8/4281 600/445
2011/0306886 A1* 12/2011 Daft .................... G01S 15/8915 600/459
2012/0197118 A1* 8/2012 Lisiecki ................... A61B 8/04 600/438
2012/0209117 A1* 8/2012 Mozes .................... G06F 3/043 600/439
2015/0018686 A1* 1/2015 Berard-Andersen ........................ A61B 8/4281 600/459
2015/0085617 A1* 3/2015 Savord ................ G01S 7/52095 367/138
2015/0133788 A1 5/2015 Mauldin
2015/0182187 A1 7/2015 Samset
2016/0136687 A1* 5/2016 Lewis, Jr. ............ B06B 1/0618 310/322
2019/0046158 A1* 2/2019 Kroon .................. A61B 8/4236
2019/0365348 A1* 12/2019 Toume ................... A61B 8/065

* cited by examiner 540
6B
522-2
510-2
542
548
546
544
522-1
510-1
6B
11
15

540
510-2
522-2
549
549
542
548
546
544
510-1
522-1
11
13

MULTI-PATCH ARRAY, ULTRASOUND SYSTEM, AND METHOD FOR OBTAINING AN EXTENDED FIELD OF VIEW

CROSS REFERENCE TO RELATED APPLICATIONS

This application is the U.S. National Phase application under 35 U.S.C. § 371 of International Application No. PCT/EP2018/051332 filed Jan. 19, 2018, published as WO 2018/134364 on Jul. 26, 2018, which claims the benefit of U.S. Patent Application No. 62/448,030 filed Jan. 19, 2017. These applications are hereby incorporated by reference herein.

RELATED APPLICATION

This application claims the benefit of and priority to U.S. application Ser. No. 62/448,030, Filed Jan. 19, 2017, which is incorporated by reference in its entirety.

TECHNICAL FIELD

This application relates to multi-patch imaging system and related methods.

BACKGROUND

Peripheral artery disease (PAD) is a common circulatory problem in which narrowed arteries reduce blood flow to the limbs. PAD leads to narrowing and hardening of the arteries. This causes decreased blood flow, which can result in pain, tissue injury and even tissue death. PAD is a common disorder that affects 8 to 12 million people in the US, especially those over 50. Besides medications, procedures such as angioplasty, stent placement, and bypass surgery may be necessary if the condition is severe (e.g., blood flow in the limb is completely or almost completely blocked). These procedures are often performed under X-ray guidance (fluoroscopy, arteriogram), which exposes the subject to radiation and lacks continuous real-time feedback.

In patients with Chronic Total Occlusions (CTO), endovascular techniques require the use of guide-wires—long metal wires less than 1 mm in diameter—to cross the CTO (see e.g., FIGS. 9A and 9B, which show x-ray images of a femoral artery 910 before and after intervention). Following successful guide-wire crossing, therapies such as balloon dilatation or atherectomy are often used to expand or clear the vessel lumen. In these patients, the blocked region 912 and the segment of the vessel distal to the blocked region cannot be visualized with arteriogram (injection of contrast dye to visualize the vessel lumen under X-Ray, as shown by FIG. 9A). The use of pre-operative images obtained from MRI/CT is a possibility, but this increases cost and has other technical challenges such as image registration. Generally, FIG. 9A illustrates the problem with navigating CTO crossings under fluoroscopy. Because a portion of the vessel is blocked prior to treatment, the blocked portion of the vessel cannot be imaged using fluoroscopy. Furthermore, repetitive or extensive X-Ray radiation to radiation is undesirable. Thus, different techniques for guidance during intervention procedures, such as CTO crossings, may be desired.

External ultrasound has been explored alternative to fluoroscopy and angiography. While ultrasound beneficially does not require radiation or use of harmful contrast agents, current ultrasound techniques require a highly-skilled sonographer to continuous maneuver and manipulate an ultrasound transducer probe in order to continually image the interventional procedure. In addition to being cumbersome, the requirement for a skilled sonographer renders ultrasound imaging impractical for CTO and other PAD interventions due to lengthy procedural times.

SUMMARY

The present invention provides systems and methods for ultrasound-guided interventional procedures. In certain aspects, the present invention provides techniques for externally imaging a vessel, which may span a distance over 10 cm, and in some cases 30 cm or more, for use in diagnosis, treatment, and monitoring of PAD and other procedures.

A multi-patch ultrasound array according to the present disclosure may include a plurality of patches of transducer elements, the plurality of patches substantially along a first axis or first direction of the array. The array may further include a frame connecting the plurality of patches such that adjacent ones of the plurality of patches are slidable relative to one another in the direction of an axis perpendicular to the first axis or direction. Each patch may include a one dimensional or a two dimensional sub-array of transducer elements.

In some embodiments, the frame may include a plurality of cells, each cell enclosing a single patch of the plurality of patches. In some embodiments, each cell and respective patch may be operatively associated with a sensor configured to provide a location of the patch relative to the cell. In some embodiments, each cell may have a width substantially the same as the width of the patch enclosed therein, and a length which is greater than the length of the patch enclosed therein. In some embodiments, each cell may include transverse sidewalls, and each patch may be frictionally retained between the transverse sidewalls of the cell enclosing the given patch. In other embodiments, each patch may form slider joints with opposite transverse sidewalls of the cell that encloses the patch.

In some embodiments, an interior of each cell may be greater than a corresponding dimension of the patch located in the cell, and cavities formed between the patch and the interior of the cell may be filled with acoustic coupling fluid. In some embodiments, each cell may include a flexible membrane along a transmission side of the array, which may enable an improved acoustic coupling between the transmission side of the array and the subject.

In some embodiments, the patches may be configured to be manually movable in relation to one another. For example, each patch may include a knob on a surface opposite a transmission surface, wherein the knob is configured to enable a user to manually slide a patch in relation to another patch. In some embodiments, the array may include a flexible membrane over a top (e.g., non-transmission side of the array), which may enable the user to manually manipulate individual patches located below the membrane, such as to adjust a location of a patch. In some embodiments, the patches may be electromechanically actuated, such as via an electromechanical actuator, a servo, or a solenoid operatively associated with each patch.

In some embodiments, the frame may include a plurality of individual housings slidably joined to one another, wherein each individual housing encloses one of the plurality of patches. In some embodiments, the individual housings may also be pivotable to one another, e.g., about an axis parallel to the elevation direction. In some embodiments, frame may be configured to be mechanically secured to a surface of a subject to be image. In some embodiments the mechanical attachment between the frame and subject may cause the array to apply sufficient pressure to the subject to minimize air pockets and thus improve acoustic coupling between the transmission side of the array and the subject. In some embodiments, the frame may be configured to be mechanically secured via an adhesive provided along the transmission side of the array. In some embodiments, the frame may be operatively associated with another mechanical attachment device such as one or more straps or a sleeve for securing the array to the subject.

An ultrasound system according to the present disclosure may include a multi-patch ultrasonic array comprising a plurality of ultrasound patches, each individually operable to transmit ultrasound toward a region of interest and receive echoes from the region of interest, wherein each patch is movable in relation to an adjacent patch in an elevation direction of the array, an ultrasound scanner configured to generate an ultrasound image from the received echoes, and a communication link configured to selectively couple each of the plurality of patches to the ultrasound scanner.

In some embodiments, the communication link may be provided by a data transfer link configured to communicatively couple multiple patches from the plurality of patches to the ultrasound scanner at any given time. In some embodiments, the communication link may be provided by a multiplexer configured to couple only one patch from the plurality of patches to the ultrasound scanner at any given time. In some embodiments, the communication link may be configured to couple one or more of the patches from the plurality of patches to the ultrasound scanner based on tracking data received from a tracking device positioned on an interventional device.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present disclosure pertains to medical ultrasound imaging and more specifically to ultrasound systems and methods which may employ a multi-patch arrays to obtain a large field of view, such as may be suitable for vascular imaging where a vessel may span a significantly larger distance than could be obtained with a single transducer probe. As described, procedures such as angioplasty, stent placement, and bypass surgery may be performed to treat PAD. These procedures are often performed under X-ray guidance (fluoroscopy, arteriogram), which exposes the subject to radiation and lacks continuous real-time feedback. Ultrasound imaging holds promise for visualizing a CTO lesion for example. However, use of ultrasound imaging is heavily dependent of the skill of the sonographer. Since the length of a CTO lesion can be 30 cm or more (in fact, almost half the diagnosed CTO lesions tend to be at least 10 cm long), the use of a single ultrasound probe can complicate clinical workflow, with a nurse/assistant needed to actively re-position the US probe to follow the progression of the wire through often highly tortuous vessel segments. The calcification within the CTO can make it hard to visualize the wire tip and it also can make probe-repositioning a difficult and time-consuming task.

Figure 1:
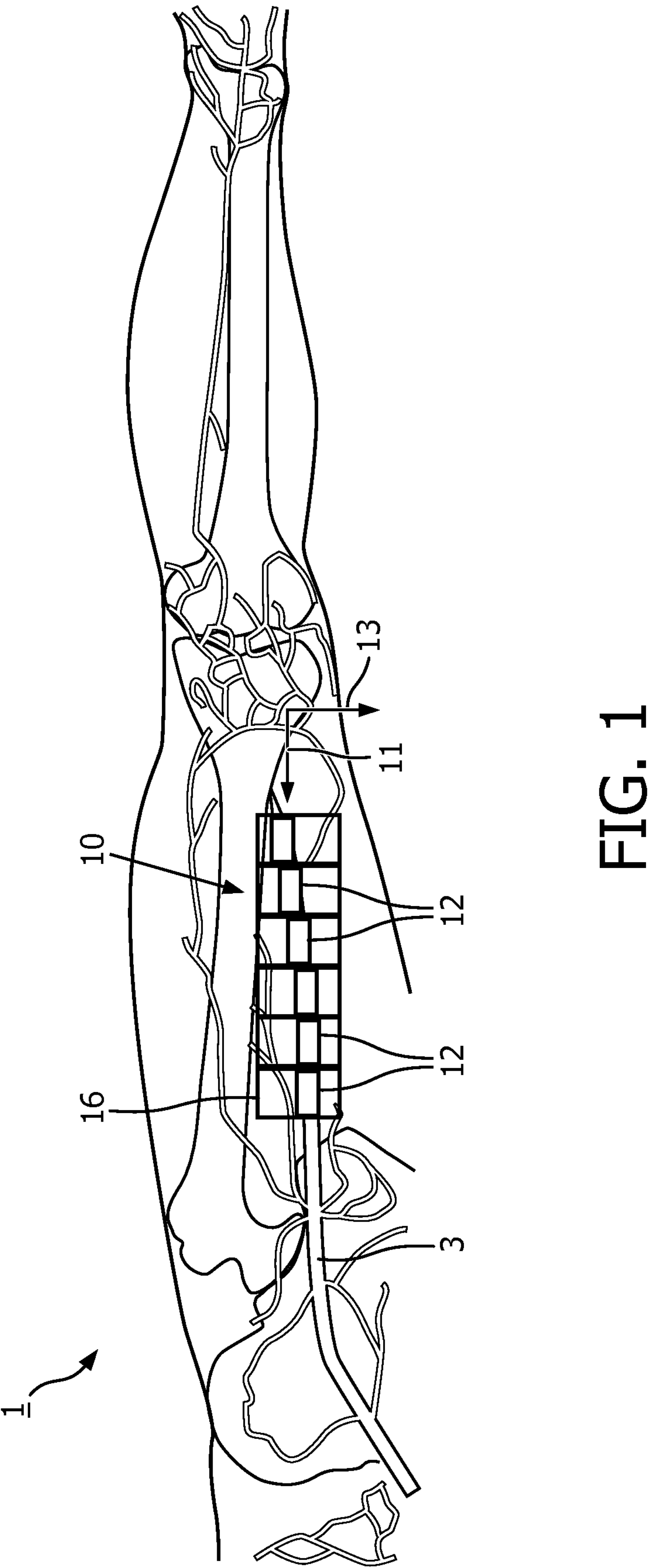
FIG. 1 is an illustration of a multi-patch array in an exemplary use scenario for imaging a femoral artery in accordance with the present disclosure.

The examples herein may obviate the need for a sonographer to move a probe while imaging a vessel. In addition, the examples herein may enable arranging the array in a manner which enables the field of view of the multi-patch array to encompass a longer span of a vessel, even in the case of tortuous vessels. For example, as shown in FIG. 1, a multi-patch array 10 may be positioned on the subject (e.g., patient 1) to image a portion of a vessel (e.g., femoral artery 3). The multi-patch array 10 includes a plurality of patches of transducer elements (in this example, six patches 12 are included in the array 10). Each patch may include a one dimensional (1D) or a two dimensional (2D) sub-array of transducer elements. The patches are arranged along a first direction 11 of the array 10. A frame 16 connects the patches 12 together to form the array 10. The frame 16 is configured to allow adjacent ones of the patches 12 to slide (i.e., move along the second direction 13) relative to one another, such as to enable the sonographer to image a larger portion of, and potentially tortuous, vessel.

Figure 2:
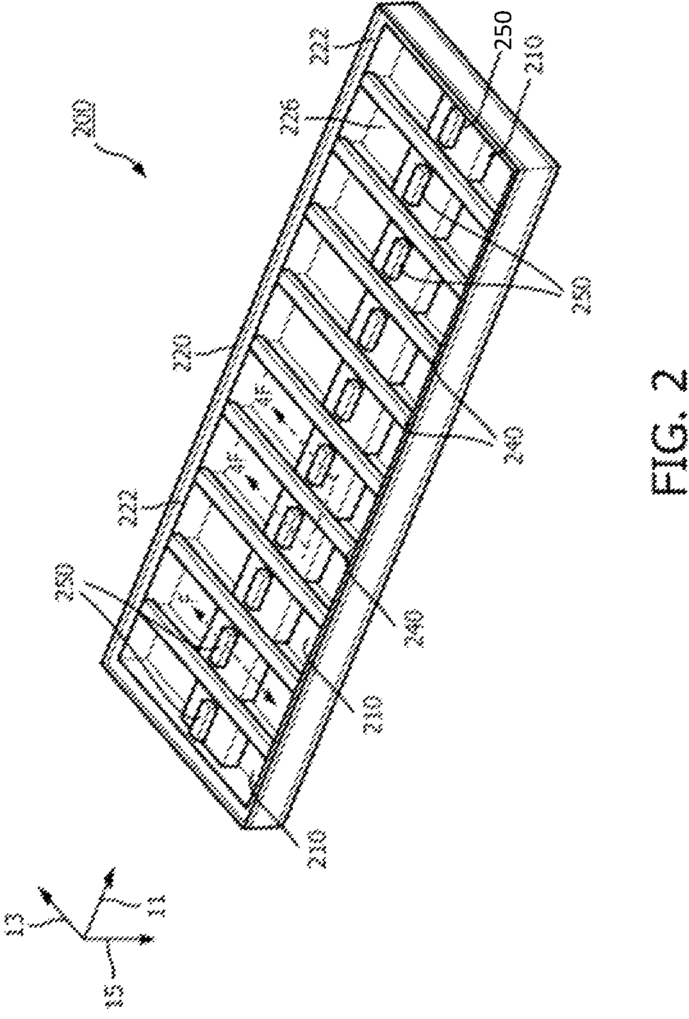
FIG. 2 is a top isometric view of a multi-patch array in accordance with an embodiment of the present disclosure.
Figure 3:
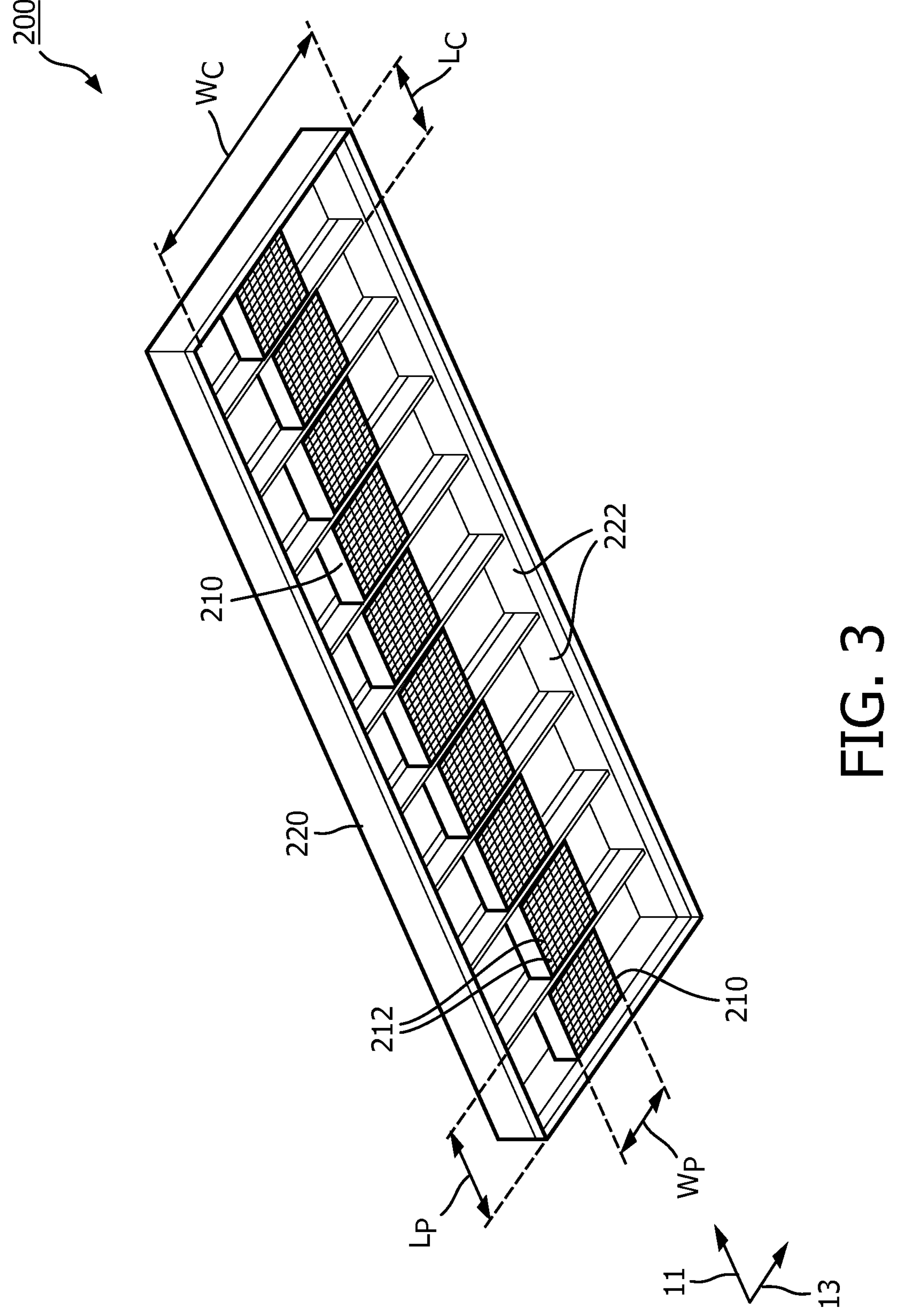
FIG. 3 is a bottom isometric view of the multi-patch array in FIG. 2.

FIGS. 2 and 3 show top and bottom views of a multi-patch array according to one embodiment. The array 200 includes a plurality of patches 210 and a frame 220. The array 200 may include any number of individual patches, for example three, four, five or more patches, 10 patches as in the illustrated example, or more. Each patch 210 may include components of ultrasonic arrays as conventionally known (e.g., a transducer stack comprising piezoelectric or CMUT elements, a backing layer which may attenuate sound in the non-transmission direction and or dissipate thermal energy, one or more matching layers and a lens on the transmission side of the sub-array). For example, each patch may include a plurality of transducer elements 212 (e.g., CMUT or piezoelectric transducer elements) arranged in a 1D or a 2D array. Beamforming and/or control of the firing of individual transducer elements may be controlled by components of an ultrasound scanner to which the array 200 is connected. The individual patches may be electrically and thus communicatively coupled to the ultrasound scanner via cables connected to an electrical connector associated with each cell and which is connected (i.e. wired) to the respective patch enclosed within each cell. The cables may connect the individual patches to a scanner via a multiplexer, as will be further described.

Each individual patch 210 may be independently operable to obtain an ultrasound image, e.g., irrespective of whether any other patch in the array 200 is active. In some embodiments, an ultrasound imaging system, which may include a scanner and the array 200, may be configured such that only a single patch of the array is active at any given time. This may reduce interference between signals transmitted from adjacent patches. In some embodiments, multiple patches may be active at any given time and the echoes detected by multiple patches may be used to form a combined image. In some examples, switching between patches (e.g., sequentially activating adjacent patches for example to image a region through which an invasive tool is advance) may be performed manually (e.g., responsive to operator input), or automatically (e.g., based on tracking data associated with the invasive tool). The images acquired from these patches can be stitched together to obtain a large field-of-view image. The relative locations of these patches e.g., for combining the sub-images, be obtained through grooves and/or sensors described later.

As shown in FIGS. 2 and 3, the individual patches 210 may be square or rectangular in shape and have a length ($L_P$) and a width ($W_P$). As such, each individual patch may provide a field of view defined by the length ($L_P$) and a width ($W_P$), thus providing an extended field of view of the array 200 having a length equal to about the length ($L_P$) multiplied by the number of patches. The individual patches 210 may have a substantially flat transmission side and may be configured as linear or phased linear arrays. In some examples, the transmission side of the patches may be curved in the elevation direction (e.g., each patch being a curvilinear sub-array) for a wider field of view in the elevation direction. The field-of-view for each patch can also be extended on the elevation direction with 2D-patch array with steerable beams (sector scan on elevation plane).

The frame 220 may include a corresponding number of cells 222, each enclosing a single patch. The cells 222 may have a square or rectangular shape and have a length ($L_C$) and a width ($W_C$) configured to accommodate the patch enclosed therein. The patches 210 are arranged side to side along a first direction (e.g., longitudinal direction 11 of the array 200). Each of the patches 210 is adjustable (e.g., slidable) at least along a second direction perpendicular to the first direction (e.g., the lateral or transverse direction 13 of the array 200). In this regard, each cell may have a length which is greater than the length of the patch enclosed therein to provide an adjustment range for the patch. For example, the individual patches may have a width Wp of 1 cm, 2 cm, 3 cm or more. The width We of each cell may be two, three, four times or more the width of the enclosed patch. The length of the cell may be about the same as the length of the patch (e.g., only slightly larger as needed for clearance and/or to accommodate components of the sliding interface 240). The frame 220 may be made from a semi-flexible material (e.g., PET or another type of plastic material) which may improve the acoustic coupling with the subject. The frame 220 may thus be configured to slightly bend (e.g., along the longitudinal direction), which may reduce the force needed to be applied to the array to acoustic couple with the subject (e.g., remove air pockets) and which may thus improve the subject's comfort during imaging. Additionally, the frame 220 may enable the individual patches to move in a third direction 15 perpendicular to the first and second directions, for example due to flexing of the frame and or pivotal coupling between adjacent patches (e.g., as described with reference to FIGS. 6A and 6B).

As described, each cell 222 of the frame 220 accommodates a single patch 210.

Figure 4A:
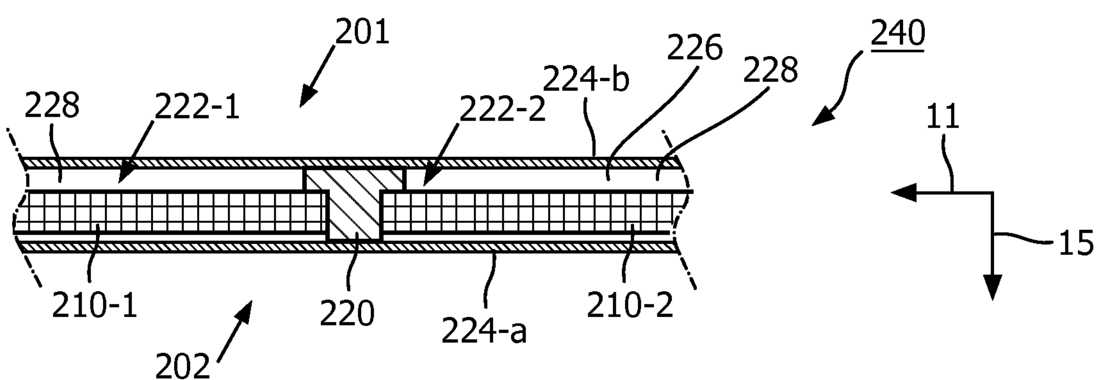
FIG. 4A-4C are simplified cross sectional views of sliding interfaces in accordance with the present disclosure.

The walls (e.g., longitudinal walls and transverse walls) of each cell define a cavity 226, which is larger than the patch accommodated therein to enable adjustability of the patch. Referring now also to FIG. 4A, the portion of the volume of the cavity 226 which is not occupied by the patch may be filled with an acoustic coupling fluid 228 (e.g., ultrasound gel). FIG. 4A shows a cross-sectional view of a sliding interface of the array 200 as indicated by line 4A-4A in FIG. 2. The cross-sectional view in FIG. 4A shows a portion of two adjacent cells 222-1 and 222-2, which enclose respective patches 210-1 and 210-2 of the array 200. As shown in FIG. 4A, the transmission side the cell (e.g., lower side 202) is sealed by a flexible membrane 224-*a*. The membrane 224-*a* may be a continuous sheet of flexible material disposed across substantially the entire transmission surface of the array. In other examples, individual membranes 224-*a* may enclose the lower sides of the individual cells. The acoustic coupling fluid 228 and flexible membrane 224-*a* provided on the transmission side may aid in acoustically coupling the transmission side (of the array 200 to the subject, e.g., by allowing the lower surface of the array to conform to the surface of the subject to be imaged.

In some examples, the upper side 201 of the cells may also be sealed by a flexible membrane 224-*b*. In some embodiments, the patches may be configured to be manually movable in relation to one another. For example, the individual patches may be manually adjustable, e.g., via the application of lateral force F on the knobs 250 (see FIG. 2). The knobs are located on the side of the patch opposite the transmission side (upper side 201) and are configured to enable a user to manually slide one patch (e.g., 210-1) in relation to another patch (e.g., 210-2). The flexible membrane 240-*b* on the upper side 201 and a shape of the knob 250 may enable the user to grasp the knobs 250 to slide the patch along the elevation direction 13. In some embodiments, the patches may instead be electromechanically actuated, for example via an electromechanical actuator, such as a servo or a solenoid operatively associated with each patch.

As shown, the array in the embodiment in FIG. 2 includes 10 patches, each of which may be about 3 cm long and about 4 cm wide, which may provide a multi-patch array with an extended field of view (FOV) of about 30 cm along the first direction 11. In other examples, different number of patches (fewer than 10 or greater than 10) may be used, each of which may have dimensions as may be appropriate for a particular application. For example, a greater number than 10 patches or longer individual patches may be used to obtain a FOV of the array 200 exceeding 30 cm. In some examples, the length of the individual patches may be two, three, four times greater than the width. In some examples, a relatively narrower patch (e.g., slightly wider than the width of vessel to be imaged, for example about 1 cm wide) may be enclosed in a wider cell (e.g., up to 10 times wider than the patch). This may provide sufficient adjustability along the length of the array to follow a curvature of a vessel, while reducing the cost of the array by virtue of reducing the overall size of the individual patches. In some examples, for example for imaging smaller subjects with smaller, more tortuous, or more densely spaced vasculature, the individual patches may be relatively smaller (e.g., shorter in length and/or in width) to enable finer adjustments for conformance with the path of a vessel to be imaged. In other examples, adjustability along other directions, such as pivotal adjustment, may also be provided for example as in the embodiment described further below with reference to FIGS. 5-6.

Figure 4B:
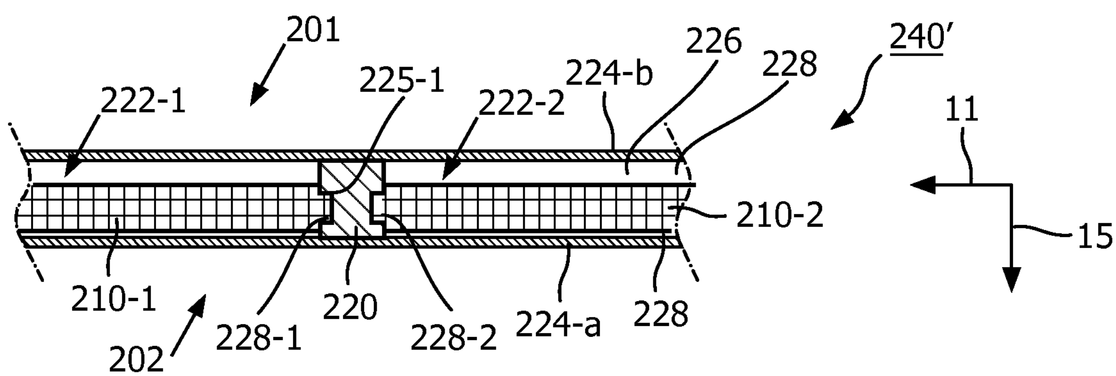

In some embodiments, such as the embodiment in FIG. 4B, the individual patches (e.g., patch 210-1 and 210-2) may be retained by friction between opposing transverse walls of the respective cell (e.g., cells 222-1 and 222-2). The patches may be sized for an interference fit with the cell—that it, the length ($L_P$) of a patch may be slightly larger than the length ($L_C$)—so that the patch is frictionally retained between opposing interference walls of a cell.

Figure 4C:
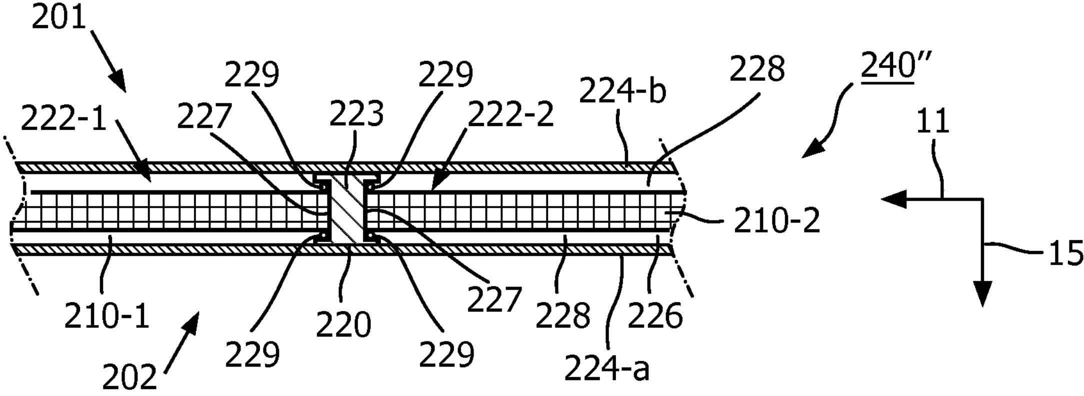

In some embodiments, the patches may form slider joints with opposite transverse sidewalls of the cell that encloses the patch. FIGS. 4B and 4C show sliding interfaces of a multi-patch array in accordance with further examples. Similar components are indicated using same reference numbers. FIG. 4B shows a cross-sectional view of a sliding interface 240' which may be used in the array 200 of FIG. 2. The cross-sectional view in FIG. 4B shows a portion of two adjacent cells 222-1 and 222-2, which enclose respective patches 210-1 and 210-2 of the array 200. In the example in FIG. 4B, each of the patches (e.g., patch 210-1 and 210-2) are slidably connected to the frame 220, and thus are slidable in relation to one another, via a tongue and groove type joint. Similar to the example in FIG. 4A, the portion of the cavities 226 not occupied by the patches is filled with an acoustic coupling fluid 228. In this embodiment, the interface wall 223 separating adjacent cells 221-1 and 222-2, includes grooves 225-1 and 225-2 configured to receive a projection 228-1, 228-2 of the respective patch. The groove and protrusion may be shaped for cooperating sliding fit and may have any suitable cross-sectional geometry (e.g., rectangular as shown, circular, dovetail, etc.). Different arrangements of grooves and protrusions than illustrated may be used. For example, the location of the protrusion and groove may be reversed (e.g., the interface wall may include a protrusion configured to engage a groove on the patch). In some embodiments, the interface wall may have a protrusion on one side and a groove on the opposite side and correspondingly, the patches may have a protrusion on one side and a groove on the other to operably engage with the interface walls. The patches may be manually adjustable (e.g., via knobs and aided by friction to maintain the patch in an adjusted position) or electromechanically actuatable (e.g., via a solenoid). Furthermore, the cells and respective patches of any of the examples herein may be operatively associated with a sensor configured to provide a location of the patch relative to the cell. The sensor may include an optical sensor (e.g., a miniature IR proximity sensor), an electromechanical, electromagnetic or capacitive sensor or another type of sensor, which may for example be arranged to measure a distance between a wall of the cell and a side of the patch or which may be arranged to measure a displacement of the patch along the length of the cell in relation to a reference position. In some examples, the sensor may include a linear encoder which may be configured to determine the position of the patch and/or provide the position to the ultrasound scanner and optionally to an actuator for electromechanically adjusting the positon of the patch.

FIG. 4C shows a cross-sectional view of another sliding interface 24" which may be used in the array 200 of FIG. 2. The cross-sectional view in FIG. 4C shows portions of the two adjacent cells 222-1 and 222-2, which enclose respective patches 210-1 and 210-2 of the array 200. Similar to the example in FIG. 4B, the portion of the cavities 226 not occupied by the patches is filled with an acoustic coupling fluid 228. In the example in FIG. 4C slidably engages the transverse wall 223 via slider joints, which include rollers 229 seated in tracks 227 on opposite sides of the wall 223. As side of each of the patches 210-1 and 210-2 is received in a respective track and sliding movement of the patches is facilitated by the rollers. Different types of slider joints or arrangements for the sliding interface may be used in other examples.

As will be appreciated, each cell of the frame has a length substantially the same as the length of the patch enclosed therein, and a width which is greater than the width of the patch enclosed therein. The term "substantially the same" encompasses lengths of a patch that are equal to or slightly greater than the length of the cell to provide sufficient frictional force to overcome a nominal force F (e.g., a force equal to the weight of the patch) thus maintaining the patch in position between the walls of the cell and yet allow the patch to be moved upon application of a force greater than the nominal force. Additionally, the term "substantially the same" encompasses lengths of a patch that are slightly smaller than the length of the cell (e.g., in the case of slider joints), the difference in length selected to minimize the gap between adjacent patches while providing sufficient clearance to allow the patch to move freely (e.g., under electromechanical actuation) in relation to the cell.

In some embodiments, frame may be configured to be mechanically secured to a surface of a subject to be image. Some embodiments the mechanical attachment between the frame and subject may cause the array to apply sufficient pressure to the subject to minimize air pockets and thus improve acoustic coupling between the transmission side of the array and the subject. For example, the frame may be provide with straps and/or enclosed within a sleeve for securing the frame to the subject. In some embodiments, the frame may be alternatively or additionally secured via an adhesive provided along the transmission side of the array.

Figure 5:
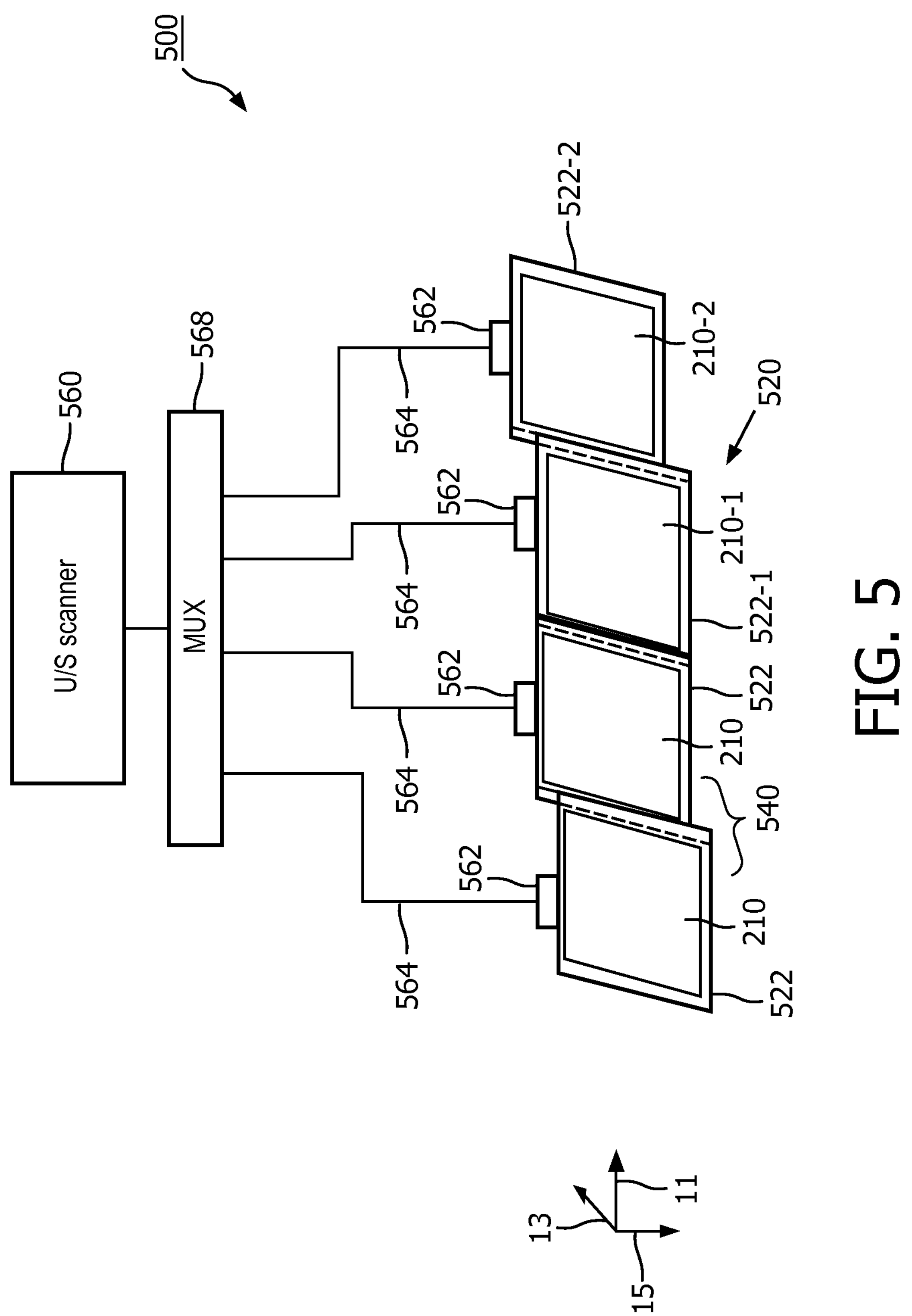
FIG. 5 is a block diagram of a multi-patch array in accordance with further embodiments of the present disclosure.

FIG. 5 shows a multi-patch array in accordance with another embodiment. The multi patch array 500 includes a plurality of patches 210 and a frame 520. The multi-patch array 500 may include one or more components similar to the array 200, which may be identified using the same reference numbers. For example, the array 500 includes individual patches 210, each of which may include a plurality of transducer elements (e.g., CMUT or piezoelectric transducer elements) arranged in a 1D or a 2D array. In contrast to the embodiment in FIG. 2 where the patches are supported by a unitary frame, in this embodiment, the individual patches are enclosed within individual housings or casings 522. Each individual casing forms a portion (e.g., a cell) of the modular frame 520. Adjacent casings (e.g., 522-1 and 522-2) are movably coupled to one another. For example, the adjacent casings (e.g., 522-1 and 522-2) are slidably coupled such that the casing and patch enclosed therein is movable in the elevation direction 13 of the array. The individual casings 522 are joined via sliding interfaces 530. As described with reference to FIG. 2, each patch is communicatively coupled to an ultrasound scanner 560 via electrical connectors 562 associated with respective cells and cables 564. In some examples, to reduce the total number of channels, individual patches 210 may be communicatively coupled to the scanner 560 through a multiplexer 568, which is configured to communicatively couple one or more, and generally fewer than all, of the individual patches 210 to the scanner 560 at any given time.

Figures 6A, 6B:
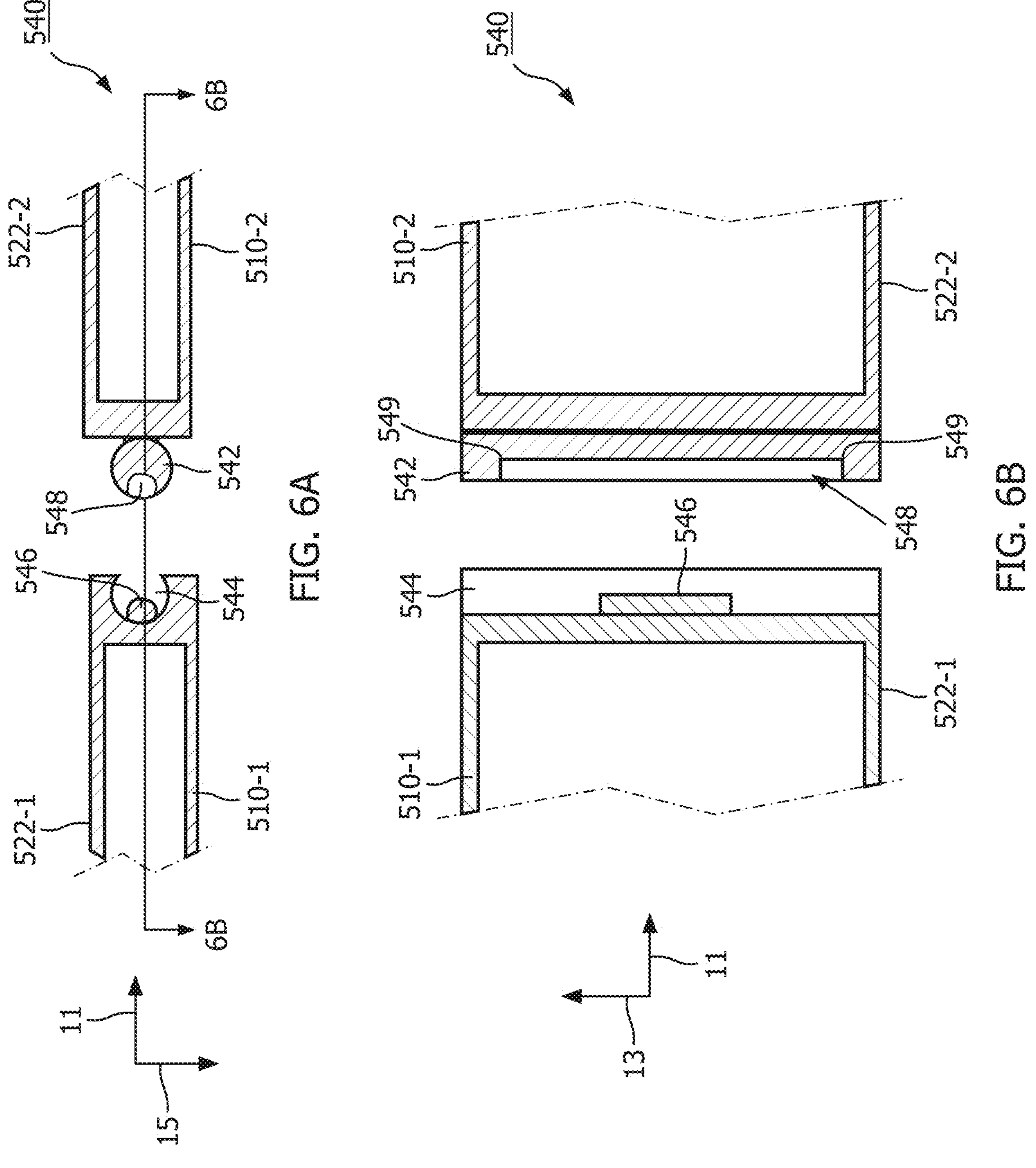
FIGS. 6A and 6B are simplified cross sectional views of another sliding interface in accordance with the present disclosure.

FIGS. 6A and 6B show simplified cross-sectional views of the sliding interface according to some examples. FIG. 6A shows a simplified cross section of the interface 540 taken at line 6A-6A in FIG. 5 and FIG. 6B shows a simplified cross section of the interface 540 taken at line 6B-6B in FIG. 6A. As shown in FIGS. 6A and 6B, in one example, the adjacent casings (e.g., 522-1 and 522-2) may be coupled using a sliding interface 540, which may be formed by a protrusion 542 (e.g., a rail) extending from the sidewall of one of the adjacent cells (e.g., casing 522-2) and a groove 544 (e.g., a track) which is formed in the sidewall of the other adjacent cell (e.g., casing 522-1) and which receives the protrusion 542. The groove and protrusion are shaped and sized to allow the two casings to translate in one degree of freedom (e.g., to slide along the direction 13) with respect to one another but remain in attachment relative to one another (e.g., restricting movement along the other two translational degrees of freedom). In some embodiments, the groove and protrusion may be shaped to also allow the two casings 522-1, 522-2, and thus the two patches 210-1, 210-2 enclosed therein, to pivot relative to one another. For example the protrusion and groove may be cylindrical in shape with the opening of the groove 544 wider than the width of the protrusion 542 at its base, thus allowing the two to not only slide but also to slightly pivot relative to one another. Relative movement of the two casings along direction 13 may be limited, for example by a hard stop incorporated in the slidable interface 540, which may also prevent the two cells from separating when being adjusted. In some examples, the hard stop may be implemented using a slot 548 in the protrusion which is capped at both ends (in some cases by removable caps 549 to enable assembly of the modular frame) and a projection 546 extending from a wall of the groove 544. The projection 546 may be shorter than the length of the slot 548 and the difference in the length of the two may determine the amount of relative movement (e.g., adjustment range) of the sliding interface 540. Different types of slidable joints may be used to implement the slidable interface between the cells.

Figure 7:
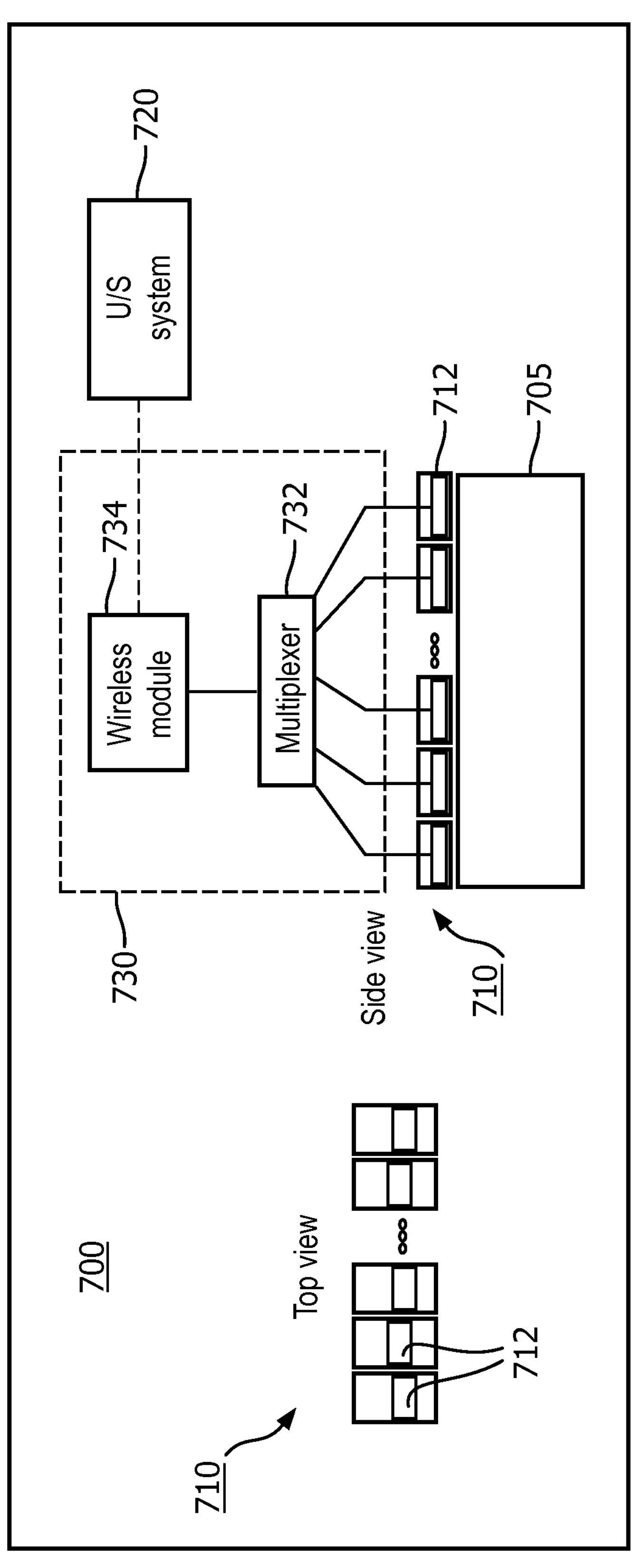
FIG. 7 is a block diagram of an ultrasound imaging system in accordance with the present disclosure.

FIG. 7 shows an ultrasound system 700 according to an embodiment of the present disclosure. The ultrasound system may include a multi-patch ultrasonic array 710 connected to an ultrasound scanner 720. The multi-patch ultrasonic array 710 may include a plurality of ultrasound patches 712 which are operable to transmit ultrasound toward a region of interest 705 and receive echoes from the region of interest 705. The individual patches 712 are movable relative to one another in the elevation direction of the array 710. For example, the array 700 may be implemented using any of the multi-patch arrays described herein (e.g., array 200, or array 500).

The ultrasound scanner 720 may include one or more components of an ultrasound imaging system (e.g., ultrasound imaging system 800 described further below with reference to FIG. 8). The ultrasound scanner 729 may be configured to generate an ultrasound image from echoes received by the multi-patch ultrasonic array 710. The ultrasound scanner 720 may be a highly portable device. For example, the ultrasound scanner 720 may be an ultrasound imaging system implemented on a hand-held device (e.g., tablet, smartphone, etc.) such as the VISIQ or LUMIFY ultrasound systems provided by PHILIPS. In some examples, the ultrasound scanner 720 may be an ultrasound imaging system implemented as a more conventional, larger but still typically portable base, which may provide a variety of imaging functions (e.g., B-mode, M-mode, color flow Doppler, PW Doppler, spectral Doppler, and other ultrasound imaging modes). For example, the ultrasound scanner 720 may be an ultrasound imaging system such as the SPARQ or EPIQ ultrasound systems provided by PHILIPS. Other ultrasound systems may be used.

The system 700 may also include a communication link 730 configured to selectively couple each of the plurality of patches to the ultrasound scanner. In some examples, the ultrasound scanner 720 may have a limited number of channels and may be configured to receive input from only a single patch of the array at any given time. In such examples, the communication link 730 may be configured to couple only a single patch of the multipatch array at any given time.

In some examples, the ultrasound scanner 720 may include high channel-count connector and may be configured to simultaneously receive echo information from multiple patches of the array. In such examples, the communication link 730 may be provided by a data transfer link configured to communicatively couple multiple patches from the plurality of patches to the ultrasound scanner 720 at any given time. For example, a parallel data link may be used to simultaneously transmit data from multiple patches. In some examples, the array 710 may be wirelessly coupled to the ultrasound scanner 720, such as via a wireless communication interface 734. In some examples, the communication link 730 may include a multiplexer 732 (MUX). The multiplexer 732 may be connected to each of the individual patches (via a wired or wireless connection) and may be configured to perform a switching function to selectively couple one or a subset of the plurality of patches 712 to the ultrasound scanner 720 at any given time. As illustrated, the multiplexer 732 may be connected via a wired or wireless connection to the ultrasound scanner 720 and transmit echo information form an active patch to the ultrasound scanner 720.

In some embodiments, the communication link may be configured to couple one or more of the patches from the plurality of patches to the ultrasound scanner based on tracking data received from a tracking device positioned on an interventional device. The tracking data may be provided by an in-situ ultrasonic tracking system, an electromagnetic (EM) tracking system, or another type of tracking technology currently known or later developed. For example, an optional in-situ tracking system, e.g., as describe in U.S. patent application Ser. No. 13/643,374, entitled "Ultrasonic tracking of ultrasound transducer(s) aboard an intervention tool," the disclosure of which is incorporate herein by reference in its entirety for any purpose, may be operatively associated with the system X to provide tracking information to the scanner. In an example, the ultrasound tracking technology may estimate the position of a passive ultrasound sensor (e.g., PZT, PVDF, copolymer or other piezoelectric material) in the field of view (FOV) of a an ultrasound transducer probe by analyzing the signal received by the tracking sensor as the beams of the imaging probe sweep the FOV. Time-of-flight measurements may provide the axial/radial distance of the PZT sensor from the imaging array, while amplitude measurements and knowledge of the beam firing sequence may provide the lateral/angular position of the sensor. When used with 3D transducers (i.e., 2D matrix arrays), the elevational position of the tracking sensor can also be obtained in a similar manner. Therefore, the 3D position of the tracking sensor can be estimated in real-time, provided it is present within the FOV of the imaging probe. The tracking sensor can be deposited on any interventional instrument such as needles, cannulas, catheters, guidewires etc. In the context of the present disclosure, the ultrasound system may be configured to receive the tracking information and activate a specific one of the patches which is determined to include the tracking sensor within its field of view.

Figure 8:
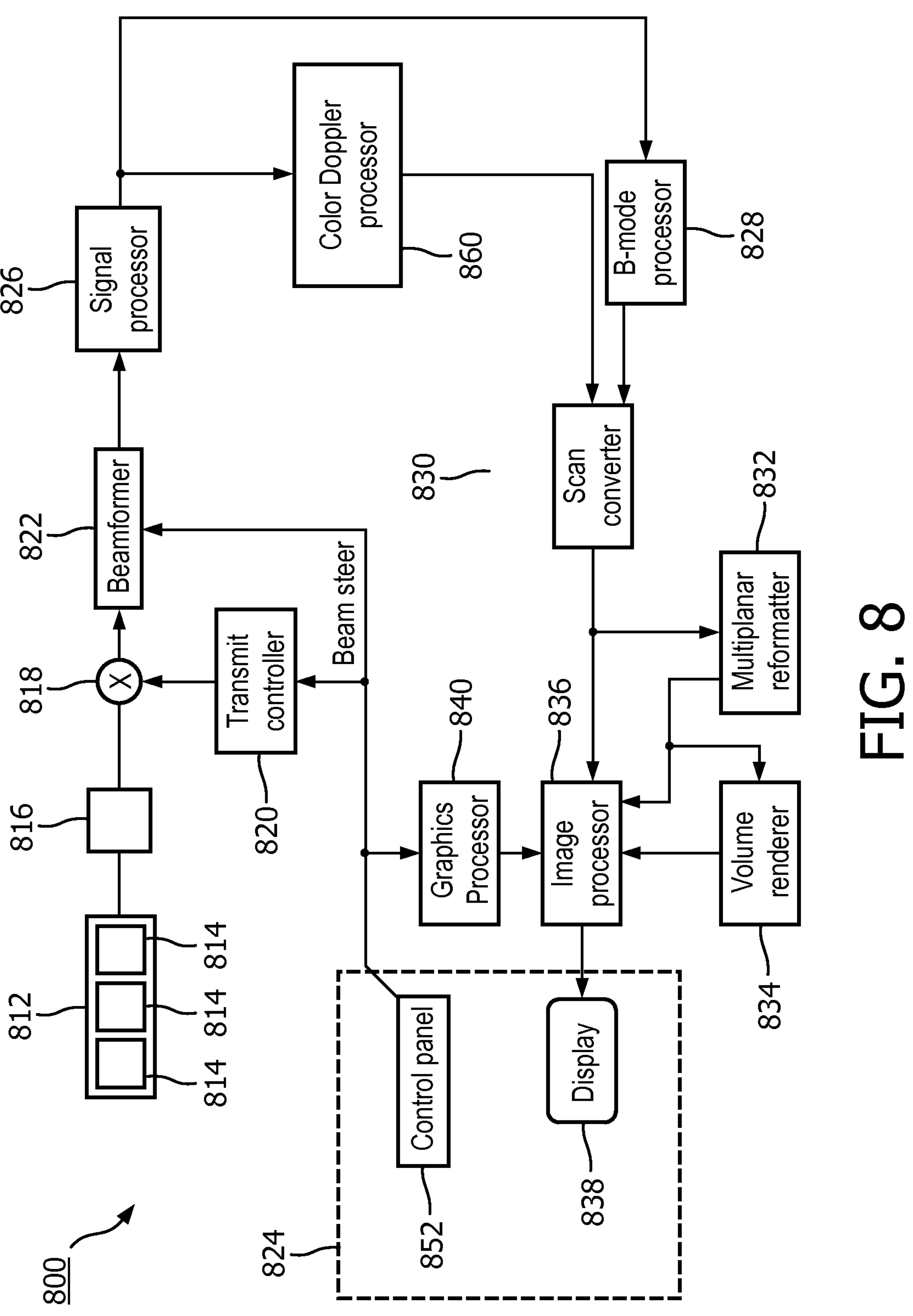
FIG. 8 is another block diagram of an ultrasound imaging system in accordance with the present disclosure.
Figure 9B:
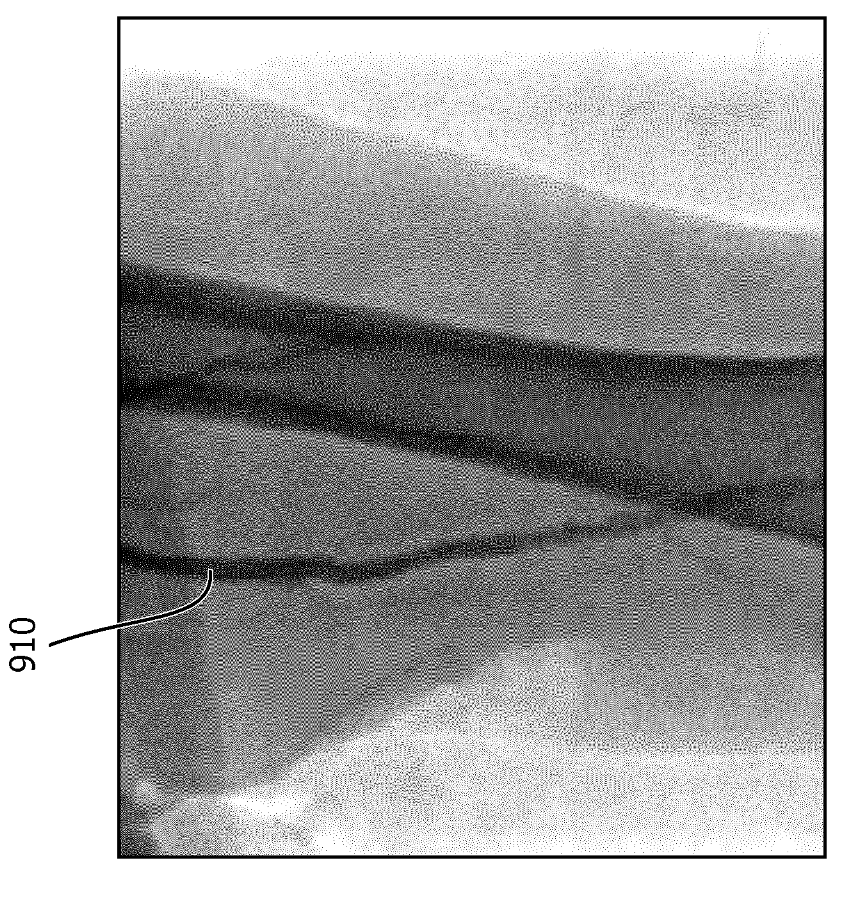
FIGS. 9A and 9B show x-ray images of a femoral artery before and after intervention.
Figure 9A:
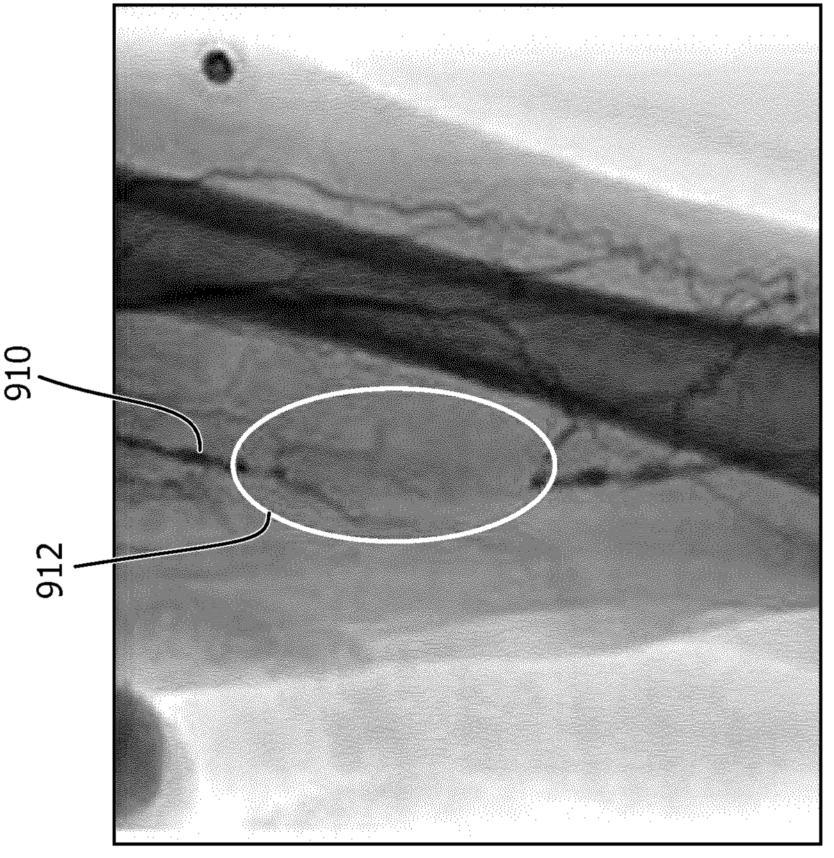

FIG. 8 shows a block diagram of an ultrasound imaging system 800 constructed in accordance with the principles of the present disclosure. The ultrasound imaging system 800 may be configured to perform B-mode imaging, Doppler imaging, and combinations of the two.

The ultrasound imaging system 800 in the embodiment in FIG. 8 may be connected to a multi-patch array 812 which includes a plurality of patches 814 slidable relative to one another. As described, each individual patch may be configured for transmitting ultrasound waves and receiving echo information. A variety of transducer arrays may be used for each of the patches 814, e.g., linear arrays, curved arrays, or phased arrays. Individual patches 814 may include, for example, a two dimensional array of transducer elements capable of scanning in both elevation and azimuth dimensions for 2D and/or 3D imaging. The patches 814 may be coupled to microbeamformers, which may be located on the array 812 or in the ultrasound system base, which may control the transmission and reception of signals by the sub-arrays of each patch. The array 812 may be coupled to the ultrasound system base via a multiplexer 816 which may be coupled (via a wired or wireless connection) to a transmit/receive (T/R) switch 818 in the base. The multiplexer may selectively couple one or more of the patches 814 to the base (e.g., to the beamformer 822). The T/R switch 818 may be configured to switch between transmission and reception, e.g., to protect the main beamformer 822 from high energy transmit signals. In some embodiments, the functionality of the T/R switch 818 and other elements in the system may be incorporated in the multiplexer 816. The ultrasound system base typically includes software and hardware components including circuitry for signal processing and image data generation as well as executable instructions for providing a user interface.

The transmission of ultrasonic pulses from the array of an active patch 814 may be directed by the transmit controller 820 coupled to the T/R switch 818 and the beamformer 822, which may receive input from the user's operation of a user interface 824. The user interface 824 may include one or more input devices such as a control panel 852, which may include one or more mechanical controls (e.g., buttons, encoders, etc.), touch sensitive controls (e.g., a trackpad, a touchscreen, or the like), and other known input devices. Another function which may be controlled by the transmit controller 820 is the direction in which beams are steered. Beams may be steered straight ahead from (orthogonal to) the transmission side of the array 812, or at different angles for a wider field of view. The beamformer 822 may combine partially beamformed signals from groups of transducer elements of the individual patches into a fully beamformed signal. The beamformed signals may be coupled to a signal processor 826.

The signal processor 826 can process the received echo signals in various ways, such as bandpass filtering, decimation, I and Q component separation, and harmonic signal separation. The signal processor 826 may also perform additional signal enhancement such as speckle reduction, signal compounding, and noise elimination. The processed signals may be coupled to a B-mode processor 828 for producing B-mode image data. The B-mode processor can employ amplitude detection for the imaging of structures in the body. The signals produced by the B-mode processor 828 may be coupled to a scan converter 830 and a multiplanar reformatter 832. The scan converter 830 is configured to arrange the echo signals in the spatial relationship from which they were received in a desired image format. For instance, the scan converter 830 may arrange the echo signal into a two dimensional (2D) sector-shaped format, or a pyramidal or otherwise shaped three dimensional (3D) format. The multiplanar reformatter 832 can convert echoes which are received from points in a common plane in a volumetric region of the body into an ultrasonic image (e.g., a B-mode image) of that plane, for example as described in U.S. Pat. No. 6,443,896 (Detmer). A volume renderer 834 may generate an image of the 3D dataset as viewed from a given reference point, e.g., as described in U.S. Pat. No. 6,530,885 (Entrekin et al.).

Additionally, the signals from the signal processor 826 may be coupled to a Doppler processor 860, which may be configured to estimate the Doppler shift and generate Doppler image data. The Doppler image data may include color data which is then overlaid with B-mode (or grayscale) image data for display. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, is then coupled the scan converter 830 where the Doppler image data is converted to the desired image format and overlaid on the B mode image of the tissue structure containing the blood flow to form a color Doppler image.

Output (e.g., images) from the scan converter 830, the multiplanar reformatter 832, and/or the volume renderer 834 may be coupled to an image processor 836 for further enhancement, buffering and temporary storage before being displayed on an image display 838. A graphics processor 840 may generate graphic overlays for display with the images. These graphic overlays can contain, e.g., standard identifying information such as patient name, date and time of the image, imaging parameters, and the like. For these purposes the graphics processor may be configured to receive input from the user interface 824, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor.

As will be appreciated, examples in accordance with the principles of this invention may provide a large field of view via an imaging modality typically adapted for much smaller fields of view (e.g., a maximum of 4 cm). The resulting field of view obtainable in accordance with the present examples may be 10 cm or greater, and in some examples up to 30 cm or greater depending on the number of individually movable patches. As described, a field of view of a multi-patch array according to the present disclosure may be adjustable to the curvature of a vessel. As described, each patch may be independently controlled so that the vessel is in the field of view. The selection of an active patch and/or the position of the patches relative to one another can be manually adjusted by the user (e.g., clinician, sonographer, registered vascular technologist) or automatically adjusted responsive to commands from the imaging base. For the latter, adjustments may be based on tracking input, feedback from image segmentation of the vessels, or location of the neighboring patches. In one embodiment, a multi-patch array, including, for example, 2-6 patches, covering an area of approximately $6\times25$ $cm^2$, may be implemented in accordance with the examples herein. As described, each individual patch may include capacitive micromachined ultrasonic transducer (CMUT) elements, piezoelectric transducer elements, or other type of ultrasonic transducer elements currently known or later developed.

A processes for imaging with a multi-patch array may include positioning the array with a plurality of adjustable patches on a subject, adjusting a location of one or more individual patches by sliding the one or more patches in the elevation direction of the array, transmitting ultrasound and receiving echoes using at least one of the plurality of patches, and displaying an image responsive to the echoes on a display of an ultrasound scanner. In some embodiment, the process may also include selectively activating and deactivating patches of the array to image a region of the subject which includes the intervention tool.

Each of the patches in the array may be positioned, manually or electronically, such that the field of view of the individual patches includes the vessel. This can be done prior to an intervention procedure and any images acquired at this stage can be used as reference images (e.g., a vessel model) during the intervention procedure. During the procedure, most of the patches are inactive (in the case where a single or a small number of patches are able to transmit images at any given time). One or more, but fewer than all, patches which are located closest to the entry location of the intervention tool are activated. As the tool advances in the vessel, activation of successive patches in the direction of tool advancement, and deactivation of patches at the opposite end, may occur responsive to user input or automatically responsive to commands from the ultrasound scanner. The commands to selectively activate/deactivate patches may be generated responsive to tracking information from a tracking sensor positioned on the intervention tool. In some examples, the commands to selectively activate/deactivate patches may additionally or alternatively be generated responsive to information about the location of the intervention tool which be obtained from image processing. For example, segmentation may be performed on the images from the active patches to determine whether the tip of the tool is within the field of view of any of the active patches. For example, if the tip of the tool is determined not to be in the FOV of the forward most patch, the ultrasound system may determine that the tip of the tool has advanced too far into the vessel to be imaged by a currently active patch and the patch next to the forward most patch may be activated. Optionally, e.g., to reduce graphics processing resources, the aft most patch may be deactivated. This procedure is repeated until the intervention procedure (e.g., CTO crossing) is completed.

In some examples, for example when using in-situ tracking, the patches may be positioned such that the signal from the tracking sensor on the intervention tool is detected to be the strongest. For example, this may be performed by moving a given patch through the adjustment range of the cell, recording a tracking signal and corresponding patch location at each step and determining the location at which the strongest tracking signal was recording then positioning the patch at the location corresponding to the strongest signal. In some examples, the patches may initially be positioned such that each patch is displaced by a predetermined amount (e.g., 1-3 mm to either side of the preceding patch). This may be a suitable initial arrangement of the patches since extreme curvatures are typically not expected in a blood vessel. Adjustments can then subsequently be made during imaging to position the patches to more optimally capture the vessel (e.g., to include as much of the vessel in the FOV and/or receive a strong a signal as possible from a tracking sensor, if used).

As will be appreciated, one or more benefits may be achieved by the present invention. For example, because the present disclosure proposes the use of ultrasound instead of X-Ray, which is the typical modality for imaging larger areas such as may be needed for PAD diagnosis or treatment, harmful X-Ray exposure is limited and potentially eliminated in accordance with the examples herein. Furthermore, the present disclosure may improve the visualization of vessels including in Chronic Total Occlusion, where blocked arteries and thus the “pathway” for the crossing wire and catheter to take, cannot be visualized under X-Ray arteriogram. The invention may also provide additional information of depth (volumetric imaging) as well as blood flow (Doppler) as compared to 2D view of arteriogram. Current technology lacks real-time feedback for the advancement of the interventional device (guide-wire, catheter) in the occluded vessel. The present invention may also improve the workflow by minimizing the need for a skillful sonographer or radiology technicians to capture X-ray images or ultrasound panoramic view throughout the interventional procedures and post-procedure evaluation. Further improvements in the imaging and the workflow may be achieved from optional in-situ tracking of the intervention device. It will be understood that the embodiments herein need not provide some or any of these benefits.

In various embodiments where components, systems and/or methods are implemented using a programmable device, such as a computer-based system or programmable logic, it should be appreciated that the above-described systems and methods can be implemented using any of various known or later developed programming languages, such as “C”, “C++ ”, “FORTRAN”, “Pascal”, “VHDL” and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A multi-patch ultrasonic array defining a first axis and a second axis perpendicular to the first axis, the array comprising:

a transmission direction;

a plurality of patches of transducer elements, the plurality of patches arranged substantially along the first axis of the array;

a frame connecting the plurality of patches wherein adjacent patches of the plurality of patches are slidable relative to one another in the direction of the second axis; and wherein the first and second axes of the array are substantially perpendicular to the transmission direction of the array.

2. The ultrasonic array of claim 1, wherein the frame comprises a plurality of cells, each cell enclosing a single patch of the plurality of patches.

3. The ultrasonic array of claim 2, wherein each of the plurality of cells and its respective patch is operatively associated with a sensor configured to provide a location of the patch relative to the cell.

4. The ultrasonic array of claim 2, wherein each cell has a length substantially the same as a length of the respective patch enclosed therein, and wherein the cell has a width which is greater than a width of the respective patch enclosed therein.

5. The ultrasonic array of claim 2, wherein each of the plurality of cells comprises transverse sidewalls and wherein each patch forms slider joints with opposite transverse sidewalls of a respective cell.

6. The ultrasonic array of claim 2, wherein an interior of each of the plurality of cells is greater than a corresponding dimension of the respective patch located in the cell, and wherein cavities formed between the respective patch and the interior of each of the plurality of cells is filled with acoustic coupling fluid.

7. The ultrasonic array of claim 2, wherein each cell comprises a flexible membrane along a transmission side of the array.

8. The ultrasonic array of claim 1, wherein each of the plurality of patches are configured to be manually movable in relation to one another.

9. The ultrasonic array of claim 8, wherein each of the plurality of patches includes a knob on a surface opposite a transmission surface, wherein the knob is configured to enable a user to manually slide at least one of the plurality of patches in relation to another of the plurality of patches.

10. The ultrasonic array of claim 1, wherein each of the plurality of patches are electromechanically actuated.

11. The ultrasonic array of claim 1, wherein each of the plurality of patches comprises a one dimensional or a two dimensional sub-array of transducer elements.

12. The ultrasonic array of claim 1, wherein the frame comprises a plurality of individual housings slidably joined to one another, wherein each of the plurality of individual housings encloses one of the plurality of patches.

13. The ultrasonic array of claim 12, wherein the plurality of individual housings are pivotable to one another about an axis parallel to the second axis.

14. The ultrasonic array of claim 1, wherein the frame is configured to be mechanically secured to a surface of a subject to be imaged.

15. The ultrasonic array of claim 14, wherein the frame is configured to be mechanically secured via an adhesive along a transmission side of the array.

16. An ultrasound imaging system for providing a large field of view along a blood vessel, the system comprising:

a multi-patch ultrasonic array comprising a transmission direction and a plurality of ultrasound patches of transducer elements arranged substantially along a first axis of the array arranged along the blood vessel, wherein each patch of the plurality of ultrasound patches is individually operable to transmit signals toward and receive signals from the blood vessel, and wherein each patch of the plurality of ultrasound patches is slidable relative to an adjacent patch along a second axis of the array perpendicular to the first axis to customize a field of view of the array to follow along the blood vessel;

wherein the first and second axes are substantially perpendicular to the transmission direction of the array;

a frame connecting the plurality of ultrasound patches;

an ultrasound scanner configured to generate an ultrasound image of at least a portion of the field of view from the received signals; and a communication link configured to selectively couple each of the plurality of patches to the ultrasound scanner.

17. The system of claim 16, wherein the communication link comprises a data transfer link configured to communicatively couple multiple patches from the plurality of patches to the ultrasound scanner at any given time.

18. The system of claim 16, wherein the communication link comprises a multiplexer configured to couple only one patch from the plurality of patches to the ultrasound scanner at any given time.

19. The system of claim 16, wherein the communication link is configured to couple one or more of the patches from the plurality of patches to the ultrasound scanner based on tracking data received from a tracking device positioned on an interventional device.

20. A multi-patch ultrasonic array configured to transmit ultrasound toward a region of interest in a transmission direction and defining a first axis and a second axis perpendicular to the first axis, the array comprising:

a plurality of patches of transducer elements, the plurality of patches arranged substantially along the first axis of the array;

a frame connecting the plurality of patches wherein adjacent patches are slidable relative to one another in the direction of the second axis, each of said first axis and said second axis being substantially perpendicular to the transmission direction.

* * * * *